United States Patent [19]

Lautenschläger et al.

[11] Patent Number: 4,599,205

[45] Date of Patent: Jul. 8, 1986

[54] 1-O-ALKYL-3-AMINO-PROPAN-1.2-DIOL-2-O-PHOSPHOLIPIDS

[75] Inventors: Hans-Heiner Lautenschläger, Pulheim-Stommeln; Michael J. Parnham, Cologne; Gerrit Prop, Pulheim, all of Fed. Rep. of Germany

[73] Assignee: A. Nattermann & Cie GmbH, Cologne, Fed. Rep. of Germany

[21] Appl. No.: 624,004

[22] Filed: Jun. 25, 1984

[30] Foreign Application Priority Data

Jul. 2, 1983 [DE] Fed. Rep. of Germany ....... 3323871

[51] Int. Cl.$^4$ ................................................ C07F 9/10
[52] U.S. Cl. .................................. 558/170; 558/172; 558/174
[58] Field of Search ........................................ 260/925

[56] References Cited

PUBLICATIONS

Synthesis, Feb. 1983, pp. 117 to 119.
H. K. Mangold, Angew, Chem. 91, 550, 554 (1979).
H. Eibl, Chemistry and Physics of Lipids, 26 (1980), pp. 405, 416.

Primary Examiner—Anton H. Sutto
Attorney, Agent, or Firm—Pearne, Gordon, Sessions, McCoy, Granger & Tilberry

[57] ABSTRACT

The invention is related to 1-O-alkyl-3-amino-propan-1.2-diol-2-O-phospholipids having the formula I

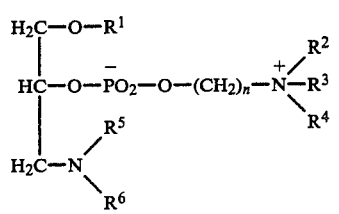

2 Claims, No Drawings

1-O-ALKYL-3-AMINO-PROPAN-1.2-DIOL-2-O-PHOSPHOLIPIDS

The present invention is related to 1-O-alkyl-3-aminopropan-1.2-diol-2-O-phospholipids. They are useful as active agents in drugs, in particular for the treatment of asthma.

The 1-O-alkyl-3-amino-propan-1.2-diol-2-O-phospholipids according to the present invention correspond to the formula I

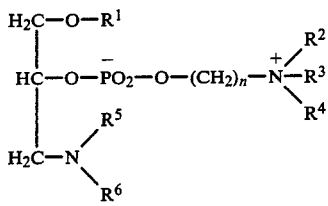

wherein $R^1$ is a member selected from the group consisting of the saturated, straight-chain alkyl groups with 10 to 20 carbon atoms, the unsaturated, straight-chain alkyl groups with 10 to 20 carbon atoms, the saturated branched alkyl groups with 10 to 20 carbon atoms and the unsaturated branched alkyl groups with 10 to 20 carbon atoms, $R^2$, $R^3$ and $R^4$ which may be the same or different from each other, represent a member selected from the group consisting of hydrogen and the lower alkyl group with 1 to 4 carbon atoms, $R^5$ and $R^6$ which may be the same or different from each other, represent a member selected from the group consisting of hydrogen, the group $-A-C_mH_{2m}-R^7$ and the group $-A-C_mH_{2m-2}-R^7$, $R^7$ is a member selected from the group consisting of hydrogen, unsubstituted phenyl and phenyl substituted by a $C_{1-3}$-alkyl, a $C_{1-3}$-alkoxy, a trifluoromethyl group or a halogen atom, A is a member selected from the group consisting of a bond and the groups —CO—, —COO— and —CONR$^8$—, $R^8$ is a member selected from the group consisting of hydrogen and $C_{1-4}$-alkyl, m is a numeral from 0 to 20 and n is a numeral from 2 to 4.

Preferred are those compounds of formula I wherein $R^1$ is a saturated straight-chained alkyl group with 10 to 20 carbon atoms or an unsaturated straight-chained alkyl group with 1 or 2 double bonds and 10 to 20 carbon atoms, $R^2$, $R^3$ and $R^4$ which may be the same or different from each other, represent hydrogen or a methyl group, $R^5$ and $R^6$ which may be the same or different from each other, represent hydrogen or the group $-A-(CH_2)_m-R^7$, $R^7$ is hydrogen, unsubstituted phenyl or phenyl substituted by a methyl, methoxy or trifluoromethyl group or a halogen atom, A represents a bond, —CO—, —COO— or —CONR$^8$—, $R^8$ is hydrogen or $C_{1-4}$-alkyl, m is an integer from 0 to 20, if $R^7$ is hydrogen, or is an integer from 0 to 2, if $R^7$ is phenyl unsubstituted or substituted as indicated, and n is 2. Most preferred under those compounds are the compounds of formula I wherein $R^1$ is a saturated straight-chained alkyl group having from 10 to 20 carbon atoms while $R^2$, $R^3$, $R^4$, $R^5$, $R^6$, $R^7$, $R^8$, m and n have the same meaning as indicated in connection with the preferred group of compounds.

Compounds according to the present invention are for instance:

3-Amino-1-O-decyl-propan-1.2-diol-2-O-phosphocholine
3-Amino-1-O-undecyl-propan-1.2-diol-2-O-phosphocholine
3-Amino-1-O-dodecyl-propan-1.2-diol-2-O-phosphocholine
3-Amino-1-O-tridecyl-propan-1.2-diol-2-O-phosphocholine
3-Amino-1-O-tetradecyl-propan-1.2-diol-2-O-phosphocholine
3-Amino-1-O-pentadecyl-propan-1.2-diol-2-O-phosphocholine
3-Amino-1-O-hexadecyl-propan-1.2-diol-2-O-phosphocholine
3-Amino-1-O-heptadecyl-propan-1.2-diol-2-O-phosphocholine
3-Amino-1-O-octadecyl-propan-1.2-diol-2-O-phosphocholine
3-Amino-1-O-nonadecyl-propan-1.2-diol-2-O-phosphocholine
3-Amino-1-O-eicosyl-propan-1.2-diol-2-O-phosphocholine
1-O-Decyl-3-methylamino-propan-1.2-diol-2-O-phosphocholine
1-O-Dodecyl-3-methylamino-propan-1.2-diol-2-O-phosphocholine
3-Methylamino-1-O-tetradecyl-propan-1.2-diol-2-O-phosphocholine
1-O-Hexadecyl-3-methylamino-propan-1.2-diol-2-O-phosphocholine
3-Methylamino-1-O-octadecyl-propan-1.2-diol-2-O-phosphocholine
1-O-Eicosyl-3-methylamino-propan-1.2-diol-2-O-phosphocholine
1-O-Decyl-3-ethylamino-propan-1.2-diol-2-O-phosphocholine
1-O-Dodecyl-3-ethylamino-propan-1.2-diol-2-O-phosphocholine
3-Ethylamino-1-O-tetradecyl-propan-1.2-diol-2-O-phosphocholine
3-Ethylamino-1-O-hexadecyl-propan-1.2-diol-2-O-phosphocholine
3-Ethylamino-1-O-octadecyl-propan-1.2-diol-2-O-phosphocholine
1-O-Eicosyl-3-ethylamino-propan-1.2-diol-2-O-phosphocholine
1-O-Decyl-3-hexadecylamino-propan-1.2-diol-2-O-phosphocholine
1-O-Dodecyl-3-hexadecylamino-propan-1.2-diol-2-O-phosphocholine
3-Hexadecylamino-1-O-tetradecyl-propan-1.2-diol-2-O-phosphocholine
1-O-Hexadecyl-3-hexadecylamino-propan-1.2-diol-2-O-phosphocholine
3-Hexadecylamino-1-O-octadecyl-propan-1.2-diol-2-O-phosphocholine
1-O-Eicosyl-3-hexadecylamino-propan-1.2-diol-2-O-phosphocholine
1-O-Decyl-3-octadecylamino-propan-1.2-diol-2-O-phosphocholine
1-O-Dodecyl-3-octadecylamino-propan-1.2-diol-2-O-phosphocholine
3-Octadecylamino-1-O-tetradecyl-propan-1.2-diol-2-O-phosphocholine 1-O-Octadecyl-3-octadecylamino-propan-1.2-diol-2-O-phosphocholine
1-O-Eicosyl-3-octadecylamino-propan-1.2-diol-2-O-phosphocholine
1-O-Decyl-3-eicosylamino-propan-1.2-diol-2-O-phosphocholine
1-O-Dodecyl-3-eicosylamino-propan-1.2-diol-2-O-phosphocholine
3-Eicosylamino-1-O-tetradecyl-propan-1.2-diol-2-O-phosphocholine
3-Eicosylamino-1-O-octadecyl-propan-1.2-diol-2-O-phosphocholine
1-O-Eicosyl-3-eicosylamino-propan-1.2-diol-2-O-phosphocholine
3-Benzylamino-1-O-decyl-propan-1.2-diol-2-O-phosphocholine
3-Benzylamino-1-O-dodecyl-propan-1.2-diol-2-O-phosphocholine
3-Benzylamino-1-O-tetradecyl-propan-1.2-diol-2-O-phosphocholine
3-Benzylamino-1-O-hexadecyl-propan-1.2-diol-2-O-phosphocholine
3-Benzylamino-1-O-octadecyl-propan-1.2-diol-2-O-phosphocholine
3-Benzylamino-1-O-eicosyl-propan-1.2-diol-2-O-phosphocholine
1-O-Hexadecyl-3-phenylamino-propan-1.2-diol-2-O-phosphocholine
1-O-Octadecyl-3-phenylamino-propan-1.2-diol-2-O-phosphocholine
3-Acetylamino-1-O-decyl-propan-1.2-diol-2-O-phosphocholine
3-Acetylamino-1-O-dodecyl-propan-1.2-diol-2-O-phosphocholine
3-Acetylamino-1-O-tetradecyl-propan-1.2-diol-2-O-phosphocholine
3-Acetylamino-1-O-hexadecyl-propan-1.2-diol-2-O-phosphocholine
3-Acetylamino-1-O-octadecyl-propan-1.2-diol-2-O-phosphocholine
3-Acetylamino-1-O-eicosyl-propan-1.2-diol-2-O-phosphocholine
3-Butyrylamino-1-O-hexadecyl-propan-1.2-diol-2-O-phosphocholine
3-Butyrylamino-1-O-octadecyl-propan-1.2-diol-2-O-phosphocholine
3-Butyrylamino-1-O-eicosyl-propan-1.2-diol-2-O-phosphocholine
1-O-Hexadecyl-3-palmitoylamino-propan-1.2-diol-2-O-phosphocholine
1-O-Octadecyl-3-palmitoylamino-propan-1.2-diol-2-O-phosphocholine
1-O-Eicosyl-3-palmitoylamino-propan-1.2-diol-2-O-phosphocholine
1-O-Hexadecyl-3-stearoylamino-propan-1.2-diol-2-O-phosphocholine
1-O-Octadecyl-3-stearoylamino-propan-1.2-diol-2-O-phosphocholine
1-O-Eicosyl-3-stearoylamino-propan-1.2-diol-2-O-phosphocholine
1-O-Hexadecyl-3-methoxycarbonylamino-propan-1.2-diol-2-O-phosphocholine
3-Methoxycarbonylamino-1-O-octadecyl-propan-1.2-diol-2-O-phosphocholine
1-O-Eicosyl-3-methoxycarbonylamino-propan-1.2diol-2-O-phosphocholine
3-Ethoxycarbonylamino-1-O-hexadecyl-propan-1.2-diol-2-O-phosphocholine
3-Ethoxycarbonylamino-1-O-octadecyl-propan-1.2-diol-2-O-phosphocholine
1-O-Eicosyl-3-ethoxycarbonylamino-propan-1.2-diol-2-O-phosphocholine
3-Benzyloxycarbonylamino-1-O-hexadecyl-propan-1.2-diol-2-O-phosphocholine
3-Benzyloxycarbonylamino-1-O-octadecyl-propan-1.2-diol-2-O-phosphocholine
3-Benzyloxycarbonylamino-1-O-eicosyl-propan-1.2-diol-2-O-phosphocholine
1-O-Hexadecyl-3-ureido-propan-1.2-diol-2-O-phosphocholine
1-O-Octadecyl-3ureido-propan-1.2-diol-2-O-phosphocholine
1-O-Eicosyl-3-ureido-propan-1.2-diol-2-O-phosphocholine
1-O-Hexadecyl-3-(3-methylureido)-propan-1.2-diol-2-O-phosphocholine
3-(3-Methylureido)-1-O-octadecyl-propan-1.2-diol-2-O-phosphocholine
1-O-Eicosyl-3-(3-methylureido)-propan-1.2-diol-2-O-phosphocholine
3-(3-Ethylureido)-1-O-hexadecyl-propan-1.2-diol-2-O-phosphocholine
3-(3-Ethylureido)-1-O-octadecyl-propan-1.2-diol-2-O-phosphocholine
1-O-Eicosyl-3-(3-ethylureido)-propan-1.2-diol-2-O-phosphocholine
1-O-Hexadecyl-3-(3-hexadecylureido)-propan-1.2-diol-2-O-phosphocholine
3-(3-Hexadecylureido)-1-O-octadecyl-propan-1.2-diol-2-O-phosphocholine
1-O-Eicosyl-3-(3-hexadecylureido)-propan-1.2-diol-2-O-phosphocholine
3-(3,3-Dimethylureido)-1-O-hexadecyl-propan-1.2-diol-2-O-phosphocholine
3-(3,3-Dimethylureido)-1-O-octadecyl-propan-1.2-diol-2-O-phosphocholine
3-(3,3-Dimethylureido)-1-O-eicosyl-propan-1.2-diol-2-O-phosphocholine
3-(3-Benzylureido)-1-O-hexadecyl-propan-1.2-diol-2-O-phosphocholine
3-(3-Benzylureido)-1-O-octadecyl-propan-1.2-diol-2-O-phosphocholine
3-(3-Benzylureido)-1-O-eicosyl-propan-1.2-diol-2-O-phosphocholine
3-(N-Acetyl-methylamino)1-O-hexadecyl-propan-1.2-diol-2-O-phosphocholine
3-(N-Acetyl-methylamino)-1-O-octadecyl-propan-1.2-diol-2-O-phosphocholine
3-(N-Acetyl-methylamino)-1-O-eicosyl-propan-1.2-diol-2-O-phosphocholine
3-(N-Acetyl-methylamino)-1-O-oleyl-propan-1.2-diol-2-O-phosphocholine
3-(N-Acetyl-methylamino)-1-O-linolyl-propan-1.2-diol-2-O-phosphocholine
3-(N-Benzoyl-methylamino)-1-O-hexadecyl-propan-1.2-diol-2-O-phosphocholin
3(N-Benzoyl-methylamino)-1-O-octadecyl-propan-1.2-diol-2-O-phosphocholin
3-(N-Benzoyl-methylamino)-1-O-eicosyl-propan-1.2-diol-2-O-phosphocholine
3-(N-Benzoyl-methylamino)-1-O-oleyl-propan-1.2-diol-2-O-phosphocholine
3-(N-Benzoyl-methylamino)-1-O-linolyl-propan-1.2-diol-2-O-phosphocholine
3-[N-(4-Chlorobenzoyl)-methylamino]-1-O-hexadecyl-propan-1.2-diol-2-O-phosphocholine 1-O-Hexadecyl-3-[N-(4-methoxybenzoyl)-methylamino]-propan-1.2-diol-2-O-phosphocholine
1-O-Hexadecyl-3[N-(4-methylbenzoyl)-methylamino]-propan-1.2-diol-2-O-phosphocholine
3-[N-(4-Ethoxybenzoyl)-methylamino]-1-O-hexadecyl-propan-1.2-diol-2-O-phosphocholine
1-O-Hexadecyl-3-[N-(3-trifluormethylbenzoyl)-methylamino]-propan-1.2-diol-2-O-phosphocholine
3-(N-Acetyl-hexadecylamino)-1-O-hexadecyl-propan-1.2-diol-2-O-phosphocholine
3-(N-Acetyl-hexadecylamino)-1-O-octadecyl-propan-1.2-diol-2-O-phosphocholine
3-(N-Acetyl-hexadecylamino)-1-O-eicosyl-propan-1.2-diol-2-O-phosphocholine
3-(N-Acetyl-benzylamino)-1-O-hexadecyl-propan-1.2-diol-2-O-phosphocholine
3-(N-Acetyl-benzylamino)-1-O-octadecyl-propan-1.2-diol-2-O-phosphocholine
3-(N-Acetyl-benzylamino)-1-O-eicosyl-propan-1.2-diol-2-O-phosphocholine
1-O-Hexadecyl-3-(N-methyl-palmitoylamino)-propan-1.2-diol-2-O-phosphocholine
3-(N-Methyl-palmitoylamino)-1-O-octadecyl-propan-1.2-diol-2-O-phosphocholine
1-O-Eicosyl-3-(N-methyl-palmitoylamino)-propan-1.2-diol-2-O-phosphocholine
3-(N-Methyl-palmitoylamino)-1-O-oleyl-propan-1.2-diol-2-O-phosphocholine
3-(N-Methyl-oleoylamino)-1-O-oleyl-propan-1.2-diol-2-O-phosphocholine
1-O-Hexadecyl-3-(N-octadecyl-oleoylamino)-propan-1.2-diol-2-O-phosphocholine
3-(N-Ethoxycarbonyl-methylamino)-1-O-hexadecyl-propan-1.2-diol-2-O-phosphocholine
3-(N-Ethoxycarbonyl-methylamino)-1-O-octadecyl-propan-1.2-diol-2-O-phosphocholine
1-O-Eicosyl-3-(N-ethoxycarbonyl-methylamino)-propan-1.2-diol-2-O-phosphocholine
3-(N-Benzyloxycarbonyl-methylamino)-1-O-hexadecyl-propan-1.2-diol-2-O-phosphocholine
3-(N-Benzyloxycarbonyl-methylamino)-1-O-octadecyl-propan-1.2-diol-2-O-phosphocholine
3-(N-Benzyloxycarbonyl-methylamino)-1-O-eicosyl-propan-1.2-diol-2-O-phosphocholine
3-(N-Benzyloxycarbonyl-hexadecylamino)-1-O-hexadecyl-propan-1.2-diol-2-O-phosphocholine
3-(N-Benzyloxycarbonyl-hexadecylamino)-1-O-octadecyl-propan-1.2-diol-2-O-phosphocholine
3-(N-Benzyloxycarbonyl-hexadecylamino)-1-O-eicosyl-propan-1.2-diol-2-O-phosphocholine
3-(N-Benzyloxycarbonyl-octadecylamino)-1-O-hexadecyl-propan-1.2-diol-2-O-phosphocholine
3-(N-Benzyloxycarbonyl-octadecylamino)-1-O-octadecyl-propan-1.2-diol-2-O-phosphocholine
3-(N-Benzyloxycarbonyl-octadecylamino)-1-O-eicosyl-propan-1.2-diol-2-O-phosphocholine
3-(N-Benzyloxycarbonyl-eicosylamino)-1-O-hexadecyl-propan-1.2-diol-2-O-phosphocholine
3-(N-Benzyloxycarbonyl-eicosylamino)-1-O-octadecyl-propan-1.2-diol-2-O-phosphocholine
3-(N-Benzyloxycarbonyl-eicosylamino)-1-O-eicosyl-propan-1 2-diol-2-O-phosphocholine
3-(N-Benzyl-benzyloxycarbonylamino)-1-O-hexadecyl-propan-1.2-diol-2-O-phosphocholine
3-(N-Benzyl-benzyloxycarbonylamino)-1-O-octadecyl-propan-1.2-diol-2-O-phosphocholine
3-(N-Benzyl-benzyloxycarbonylamino)-1-O-eicosyl-propan-1.2-diol-2-O-phosphocholine
3-(N-Benzyl-benzyloxycarbonylamino)-1-O-oleyl-propan-1.2-diol-2-O-phosphocholine
1-O-Hexadecyl-3-(1-methylureido)-propan-1.2-diol-2-O-phosphocholine
3-(1-Methylureido)-1-O-octadecyl-propan-1.2-diol-2-O-phosphocholine
1-O-Eicosyl-3-(1-methylureido)-propan-1.2-diol-2-O-phosphocholine
3-(1-Ethylureido)-1-O-hexadecyl-propan-1.2-diol-2-O-phosphocholine
3-(1-Ethylureido)-1-O-octadecyl-propan-1.2-diol-2-O-phosphocholine
1-O-Eicosyl-3-(1-ethylureido)-propan-1.2-diol-2-O-phosphocholine
1-O-Hexadecyl-3-(1-hexadecylureido)-propan-1.2-diol-2-O-phosphocholine
3-(1-Hexadecylureido)-1-O-octadecyl-propan-1.2-diol-2-O-phosphocholine
1-O-Eicosyl-3-(1-hexadecylureido)-propan-1.2-diol-2-O-phosphocholine
3-(1,3-Dimethylureido)-1-O-hexadecyl-propan-1.2-diol-2-O-phosphocholine
3-(1,3-Dimethylureido)-1-O-octadecyl-propan-1.2-diol-2-O-phosphocholine
3-(1,3-Dimethylureido)-1-O-eicosyl-propan-1.2-diol-2-O-phosphocholine
3-(1-Benzylureido)-1-O-hexadecyl-propan-1.2-diol-2-O-phosphocholine
3-(1-Benzylureido)-1-O-octadecyl-propan-1.2-diol-2-O-phosphocholine
3-(1-Benzylureido)-1-O-eicosyl-propan-1.2-diol-2-O-phosphocholine
1-O-Hexadecyl-3-(1-hexadecyl-3-methylureido)-propan-1.2-diol-2-O-phosphocholine
3-(1-Hexadecyl-3-methylureido)-1-O-octadecyl-propan-1.2-diol-2-O-phosphocholine
1-O-Eicosyl-3-(1-hexadecyl-3-methylureido)-propan-1.2-diol-2-O-phosphocholine
1-O-Hexadecyl-3-(3-methyl-1-octadecylureido)-propan-1.2-diol-2-O-phosphocholine
3-(3-Methyl-1-octadecylureido)-1-O-octadecyl-propan-1.2-diol-2-O-phosphocholine
1-O-Eicosyl-3-(3-methyl-1-octadecylureido)-propan-1.2-diol-2-O-phosphocholine
3-(3-Ethyl-1-hexadecylureido)-1-O-hexadecyl-propan-1.2-diol-2-O-phosphocholine
3-(3-Ethyl-1-hexadecylureido)-1-O-octadecyl-propan-1.2-diol-2-O-phosphocholine
1-O-Eicosyl-3-(3-ethyl-1-hexadecylureido)-propan-1.2-diol-2-O-phosphocholine
1-O-Hexadecyl-3-(1-hexadecyl-3-phenylureido)-propan-1.2-diol-2-O-phosphocholine
3-[3-(4-chlorophenyl)-1-hexadecylureido]-1-O-hexadecyl-propan-1.2-diol-2-O-phosphocholine
3-(1-Hexadecyl-3-phenylureido)-1-O-octadecyl-propan-1.2-diol-2-O-phosphocholine
1-O-Eicosyl-3-(1-hexadecyl-3-phenylureido)-propan-1.2-diol-2-O-phosphocholine
1-O-Hexadecyl-3-(3-phenylureido)-propan-1.2-diol-2-O-phosphocholine
1-O-Octadecyl-b 3-(3-phenylureido)-propan-1.2-diol-2-O-phosphocholine
1-O-Eicosyl-3-(3-phenylureido)-propan-1.2-diol-2-O-phosphocholine
3-[3-(4-chlorophenyl)-ureido]-1-O-hexadecyl-propan-1.2-diol-2-O-phosphocholine
3-[3-(4-chlorophenyl)-ureido]-1-O-octadecyl-propan-1.2-diol-2-O-phosphocholine 3-[3-(4-chlorophenyl)-ureido]-1-O-eicosyl-propan-1.2-diol-2-O-phosphocholine
1-O-Hexadecyl-3-[3-(2-phenylethyl)-ureido]-propan-1.2-diol-2-O-phosphocholine
1-O-Octadecyl-3-[3-(2-phenylethyl)-ureido]-propan-1.2-diol-2-O-phosphocholine
1-O-Eicosyl-3-[3-(2-phenylethyl)-ureido]-propan-1.2-diol-2-O-phosphocholine
1-O-Hexadecyl-3-(2-phenylethylamino)-propan-1.2-diol-2-O-phosphocholine
1-O-Octadecyl-3-(2-phenylethylamino)-propan-1.2-diol-2-O-phosphocholine
1-O-Eicosyl-3-(2-phenylethylamino)-propan-1.2-diol-2-O-phosphocholine
3-(N-Acetyl-2-phenylethylamino)-1-O-hexadecyl-propan-1.2-diol-2-O-phosphocholine
3-(N-Acetyl-2-phenylethylamino)-1-O-octadecyl-propan-1.2-diol-2-O-phosphocholine
3-(N-Acetyl-2-phenylethylamino)-1-O-eicosyl-propan-1.2-diol-2-O-phosphocholine
3-(N-Acetyl-2-phenylethylamino)-1-O-oleyl-propan-1.2-diol-2-O-phosphocholine
[1-(N-Acetyl-aminomethyl)-2-hexadecyloxy-ethyl]-3-trimethylammoniopropyl-phospate
[1-(N-Acetyl-aminomethyl)-2-hexadecyloxy-ethyl]-4-trimethylammoniobutyl-phosphate
[1-(N-Acetyl-methylaminomethyl)-2-hexadecyloxy-ethyl]-3-trimethylammoniopropyl-phosphate
[1-(N-Acetyl-methylaminomethyl)-2-hexadecyloxy-ethyl]-4-trimethylammoniobutyl-phosphate
[1-(N-Acetyl-aminomethyl)-2-octadecyloxy-ethyl]-3-trimethylammoniopropyl-phosphate
[1-(N-Acetyl-aminomethyl)-2-octadecyloxy-ethyl]-4-trimethylammoniobutyl-phosphate
[1-(N-Acetyl-methylaminomethyl)-2-octadecyloxy-ethyl]-3-trimethylammoniopropyl-phosphate
[1-(N-Acetyl-methylaminomethyl)-2-octadecyloxy-ethyl]-4-trimethylammoniobutyl-phosphate
[1-(N-Acetyl-aminomethyl)-2-hexadecyloxy-ethyl]-2-dimethylammonioethyl-phosphate
[1-(N-Acetyl-methylaminomethyl)-2-hexadecyloxy-ethyl]-2-dimethylammonioethyl-phosphate
[1-(N-Acetyl-aminomethyl)-2-octadecyloxy-ethyl]-2-dimethylammonioethyl-phosphate
[1-(N-Acetyl-methylaminomethyl)-2-octadecyloxy-ethyl]-2-dimethylammonioethyl-phosphate
[1-(N-Acetyl-aminomethyl)-2-hexadecyloxy-ethyl]-2-butyldimethylammonioethyl-phosphate
[1(N-Acetyl-aminomethyl)-2-octadecyloxy-ethyl]-2-butyldimethylammonioethyl-phosphate.

Depending upon the fact whether there has been effected a split of racemates, the above compounds may be present in their R- or S-form or as racemate mixture.

The compounds of the present invention are biologically very active and may be used for instance in drugs. Thus, they may be used for the treatment of asthma.

For preparing the new 1-O-alkyl-3-amino-propane-1.2-diol-2-O-phospholipids, 2.3-epoxypropylethers of formula

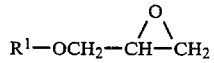

(regarding their production see E. Mouzin et al., Synthesis 1983, 117 and following) are subjected to reaction with the corresponding amine of formula

corresponding to the procedure as known for epoxides (see for instance Houben-Weyl, Methoden der organischen Chemie, 4. Ed., Vol. 11/1, p. 314 and following, Georg Thieme Verlag, Stuttgart 1957) to yield the corresponding substituted 3-amino-2-hydroxy-propylethers and, if desired, to subject them to N-acylation by usual methods. The starting materials II

wherein $R^1$, $R^5$ and $R^6$ have the same meaning as in formula I, resulting therefrom are subjected to reaction with dicholorophosphoric acid-ω-halogene alkyl esters of formula III

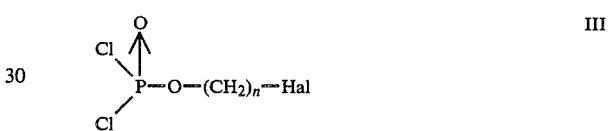

wherein n has the same meaning as in formula I and Hal is a chlorine or bromine atom, in an inert organic solvent, possibly with the addition of an auxiliary base such as pyridine or triethylamine, the resulting compounds subsequently being reacted with an amine of formula IV

wherein $R^2$, $R^3$ and $R^4$ have the same meaning as in formula I in an inert organic solvent such as toluene, dioxane, tetrahydrofurane, possibly with the application of pressure (regarding thereto, see: H. K. Mangold, Angew. Chemie 91, 550 to 560 (1979; H. Eibl, Chem. and Phys. of Lipids 26, 405 to 429 (1980)).

If the resulting compounds of formula I have benzyl, benzyloxycarbonyl or similar protective groups, these groups may be split-off by hydrogenation under usual conditions in the presence of heavy metal catalysts and hydrogen, thus forming compounds of formula I wherein $R^5$ and/or $R^6$ is hydrogen.

On the other side, a compound of formula I wherein $R^5$ and/or $R^6$ is hydrogen may be subjected to reaction, in the presence of a suitable condensation agent such as thionylchloride, carbonylbisimidazol, carbodiimides and the like, with an acid of formula V

wherein m and $R^7$ have the same meaning as in formula I, or, possibly in the presence of auxiliary basis such as triethylamine, pyridine and the like, with an acid derivative of formula VI

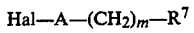
Hal—A—(CH$_2$)$_m$—R$^7$  VI wherein A, m and R$^7$ have the same meaning as in formula I (with the exception of A representing a bond) and Hal is a halogen atom or an acid anhydride group, in particular a chloro or a bromo atom. Acylation may also be effected with isocyanates of formula VII

R$^5$—N=C=O  VII wherein R$^5$ has the same meaning as in formula I, possibly with the addition of catalysts such as dimethylformamide or 4-dimethylaminopyridine.

The starting compounds of formula II may be used in their R- or S-form or as racemate; accordingly, there are obtained the R- or S-forms or racemate mixtures of the final products I.

The present invention is further related to pharmaceutical preparations which contain the 1-O-alkyl-3-amino-propan-1.2-diol-2-O-phospholipids of formula I. The pharmaceutical preparations according to the present invention are products for enteral as oral or rectal as well as parenteral application. They contain the pharmaceutically active agents alone or together with usual, pharmaceutically applicable carrier materials. Preferably, the pharmaceutical preparations of the active agent are in the form of single doses corresponding to the desired form of application such as tablets, dragees, capsules, suppositories, granulates, solutions, emulsions or suspensions. The dosages of the compounds usually are between 1 and 1000 mg. per day, preferably between 10 and 100 mg. per day, and the product may be administered once or several times, preferably between two and three times, per day.

The preparation of the compounds according to the present invention are further illustrated by the following examples. The reported melting points have been determined by means of a Büchi 510 melting point apparatus and they are not corrected. The infrared spektra have been determined in a Perkin-Elmer 257 or Nicolet NIC-3600 type apparatus.

EXAMPLE 1

3-(N-acetyl-methylamino)-1-O-hexadecyl-propan-1.2-diol-2-O-phosphocholine (a) 1-Hexadecyloxy-3-methylamino-propan-2-ol A cooled mixture of 15.5 g of methylamine, 50 cc. of tetrahydrofurane and 15 g of hexadecyl-2.3-epoxypropylether is heated to 60° C. for 2 hours in an autoclave, cooled and evaporated in a vacuo. The residue is purified by column chromatography (silicic acid gel//chloroform/methanol).

Yield: 10.5 g F.: 89° to 91° C.

(b) 3-(N-acetyl-methylamino)-1-hexadecyloxy-propan-2-ol 5 g of 1-hexadecyloxy-3-methylamino-propan-2-ol are dissolved in 30 cc. of anhydrous chloroform. At first 3 g of triethylamine and separately thereafter 2.4 g of acetylchloride are added dropwise with cooling and the mixture is stirred for 8 hours. The chloroform solution is washed with 2% hydrochloric acid and water, is evaporated and the residue is dissolved in 100 cc. of methanol. A solution of 0.6 g of sodium hydroxide in a little methanol is added to the methanol solution and the mixture is stirred at room temperature for one hour.

The solvent is evaporated in a vacuo and the residue is triturated in chloroform. The chloroform solution is washed with 2% hydrochloric acid and water, is dried over sodium sulfate and is evaporated.

Yield: 3.7 g of an oil.

IR (film): 3350, 1630 1120 cm$^{-1}$.

(c) [1-(N-acetyl-methylaminomethyl)-2-hexadecyloxyethyl]-2-bromoethyl phosphate 3.3 g of 3-(N-acetyl-methylamino)-1-hexadecyloxy-propan-2-ol are dissolved in 100 cc. of anhydrous chloroform and the solution is added dropwise to a mixture of 4.3 g of 2-bromoethylphosphoric acid dichloride, 10 cc. of chloroform and 50 cc. of pyridin cooled with ice. The resulting mixture is stirred for one hour at room temperature, diluted with water and stirred another hour at room temperature. The organic phase is separated, washed with 5% hydrochloric acid and water, dried over sodium sulfate and the solvent is separated in a vacuo. The residue is purified by column chromatography (silicic acid gel//chloroform/methanol).

Yield: 1.6 g of an oil.

(d) 3-(N-acetyl-methylamino)-1-O-hexadecyl-propan-1.2-diol-2-O-phosphocholine 1.6 g of [1-(N-acetyl-methylaminomethyl)-2-hexadecyloxyethyl]-2-bromoethyl phosphate are dissolved in 30 cc. of anhydrous toluene. About 3 cc. of a 33% solution of trimethylamine in ethanol is added thereto and the resulting mixture is stirred for 4 hours at 60° C. in a closed container. The solvent is evaporated in a vacuo and the residue is purified by column chromatography (silicic acid gel//chloroform/methanol).

Yield: 0.4 g of a waxy product.

IR (film): 1635 cm$^{-1}$.

EXAMPLE 2

3-(N-benzyl-benzyloxycarbonylamino)-1-O-hexadecyl-propan-1.2-diol-2-O-phosphocholine (a) 3-Benzylamino-1-hexadecyloxy-propan-2-ol A mixture of 24.4 g of benzylamine, 100 cc. of tetrahydrofurane and 34 g of hexadecyl-2.3-epoxypropylether is refluxed for 8 hours and the solvent is evaporated in a vacuo. The residue is recrystallized from hexane.

Yield: 30.8 g. F.: 56° to 58° C.

(b) 3-(N-benzyl-benzyloxycarbonylamino)-1-hexadecyloxy-propan-2-ol 21.4 g of 3-benzylamino-1-hexadecyloxy-propan-2-ol are dissolved in 100 cc. of anhydrous chloroform. At first 5.4 g of triethylamine and then a solution of 9 g of chloroformic acid benzyl ester in 50 cc. of chloroform is added dropwise with cooling and the mixture is stirred for 3 hours. The chloroform solution is washed with 5% hydrocholoric acid and water, dried over sodium sulfate, evaporated and the residue is purified by column chromatography (silicic acid gel//chloroform).

Yield: 21 g (oil).

IR (film): 3445, 1701, 1125 cm$^{-1}$.

(c) [1-(N-benzyl-benzyloxycarbonylaminomethyl)-2-hexadecyloxy-ethyl)]-2-bromoethyl phosphate 16 g of 3-(N-benzyl-benzyloxycarbonylamino)-1-hexadecyloxy-propan-2-ol are dissolved in 30 cc. of anhydrous chloroform and the solution is added dropwise to an ice-cooled mixture of 14.5 g of 2-bromoethylphosphoric acid dichloride, 120 cc. of chloroform and 9.5 g of pyridine. The mixture is stirred for 1 hour at room temperature, diluted with water and again stirred for 1 hour at room temperature. The organic phase is separated, washed with 5% hydrochloric acid and water, dried over sodium sulfate and the solvent is evaporated in a vacuo. The residue is purified by column chromatography (silicic acid gel//chloroform/methanol).

Yield: 11.8 g (oil).

(d) 3-(N-benzyl-benzyloxycarbonylamino)-1-O-hexadecyl-propan-1.2-diol-2-O-phosphocholine 11.5 g of [1-(N-benzyl-benzyloxycarbonylaminomethyl)-2-hexadecyloxyethyl]-2-bromoethylphosphate are dissolved in 50 cc. of anhydrous toluene. About 10 cc. of a 33% solution of trimethylamine in ethanol is added thereto and the mixture is stirred for 4 hours at 60° C. in a closed container. The solvent is evaporated in a vacuo and the residue is purified by column chromatography (silicic acid gel//chloroform/methanol).

Yield: 4.6 g of a waxy product.

IR (film): 1696 cm$^{-1}$.

EXAMPLE 3

3-Amino-1-O-hexadecyl-propan-1.2-diol-2-O-phosphocholine 4.3 g of 3-(N-benzylbenzyloxycarbonylamino)-1-O-hexadecylpropan-1.2-diol-2-O-phosphocholine are dissolved in 200 cc. of a 4:1 (v/v)-mixture of dioxane and water and, after the addition of 0.43 g of palladium-active carbon, are hydrogenated with hydrogen. The solution is filtered, the filter residue is washed with ethanol, the filtrates are combined and evaporated to dryness. The residue is purified by column chromatography (silicic acid gel//chloroform/methanol/conc. ammonia).

Yield: 1.4 g. F.: 217° to 219° C.

EXAMPLE 4

3-Benzylamino-1-O-hexadecyl-propan-1.2-diol-2-O-phosphocholine as produced similarly to Example 3 by incomplete hydrogenation For instance, there are isolated with the procedure described in Example 3 0.3 g of waxy 3-benzylamino-1-O-hexadecyl-propan-1.2-diol-2-O-phosphocholine as side product. With the same procedure there of course may be also produced the 3-alkylamino-, 3-arylamino- and 3-arylalkylamino-compounds.

EXAMPLE 5

3-Acetylamino-1-O-hexadecyl-propan-1.2-diol-2-O-phosphocholine (a) 0.35 g of 3-amino-1-O-hexadecyl-propan-1.2-diol-2-O-phosphocholine are dissolved in 10 cc. of anhydrous chloroform. 0.14 g of acetic acid anhydride are added thereto and the mixture is stirred for about 12 hours at room temperature. The solution is evaporated in a vacuo and the residue is purified by column chromatography (silicic acid gel//chloroform/methanol/water).

Yield: 0.2 g. F.: 237° to 239° C.

IR (in KBr): 1667 cm$^{-1}$.

(b) 0.24 g of 3-amino-1-O-hexadecyl-propan-1.2-diol-2-O-phosphocholine are dissolved in 5 cc. of anhydrous chloroform. 0.1 g of triethylamine and 0.08 g of acetylchloride are added thereto and the mixture is stirred for about 12 hours at room temperature. The solution is evaporated in a vacuo and the residue is purified by column chromatography (silicic acid gel//chloroform/methanol/water).

Yield: 0.18 g.

EXAMPLE 6

1-O-Hexadecyl-3-(3-methylureido)-propan-1.2-diol-2-O-phosphocholine 0.48 g of 3-amino-1-O-hexadecyl-propan-1.2-diol-2-O-phosphocholine are dissolved in 10 cc. of anhydrous chloroform. 0.17 g of methylisocyanate are added to this solution and the mixture is stirred for 12 hours at room temperature. The solution is evaporated in a vacuo and the residue is purified by column chormatography (Silicic acid gel//chloroform/methanol/water).

Yield: 0.4 g. F.: 243° to 245° C.

What we claim is:

1. 1-O-Alkyl-3-amino-propan-1.2-diol-2-O-phospholipids of the formula I $$\begin{array}{c} H_2C-O-R^1 \\ | \\ HC-O-PO_2^--O-(CH_2)_n-\overset{+}{N}\diagup\overset{R^2}{\underset{R^4}{\diagdown R^3}} \\ | \quad \diagup R^5 \\ H_2C-N \\ \diagdown R^6 \end{array} \quad I$$

wherein

R$^1$ is a member selected from the group consisting of the saturated, straight-chain alkyl groups with 10 to 20 carbon atoms, the unsaturated, straight-chain alkyl groups with 10 to 20 carbon atoms, the saturated branched alkyl groups with 10 to 20 carbon atoms and the unsaturated branched alkyl groups with 10 to 20 carbon atoms, R$^2$, R$^3$ and R$^4$ which may be the same or different from each other, represent a member selected from the group consisting of hydrogen and the lower alkyl group with 1 to 4 carbon atoms, R$^5$ and R$^6$ which may be the same or different from each other, represent a member selected from the group consisting of hydrogen, the group —A—C$_m$H$_{2m}$—R$^7$ and the group —A—C$_m$H$_{2m-2}$—R$^7$, R$^7$ is a member selected from the group consisting of hydrogen, unsubstituted phenyl and phenyl substituted by a C$_{1-3}$-alkyl, a C$_{1-3}$-alkoxy, a trifluoromethyl group or a halogen atom, A is a member selected from the group consisting of a bond and the groups —CO—, —COO— and —CONR$^8$—, R$^8$ is a member selected from the group consisting of hydrogen and C$_{1-4}$-alkyl, m is a numeral from 0 to 20 and n is a numeral from 2 to 4.

2. 1-O-Alkyl-3-amino-propan-1.2-diol-2-O-phospholipids of the formula I according to claim 1 wherein R$^1$ is a member selected from the group consisting of the saturated straight-chain alkyl groups with 10 to 20 carbon atoms and the unsaturated, straight-chain alkyl groups with 10 to 20 carbon atoms, R$^2$, R$^3$ and R$^4$ which may be the same or different from each other, represent a member selected from the group consisting of hydrogen and methyl, R$^5$ and R$^6$ which may be the same or different from each other, represent a member selected from the groups consisting of hydrogen and the group —A—(CH$_2$)$_m$—R$^7$, $R^7$ is a member selected from the group consisting of hydrogen, unsubstituted phenyl and phenyl substituted by a methyl, a methoxy, a trifluoromethyl group or a halogen atom, A is a member selected from the group consisting of a bond, and the groups —CO—, —COO— and —CONR$^8$—, $R^8$ is a member selected from the group consisting of hydrogen and $C_{1-4}$-alkyl, m is a numeral from 0 to 20, if $R^7$ is hydrogen, or is a numeral from 0 to 2, if $R^7$ is unsubstituted or substituted phenyl and n is 2.

* * * * *